(12) United States Patent
Oren

(10) Patent No.: US 9,169,178 B2
(45) Date of Patent: Oct. 27, 2015

(54) MANUFACTURING OF STABILIZED PROPARGYL BROMIDE

(71) Applicant: BROMINE COMPOUNDS LTD., Beer Sheva (IL)

(72) Inventor: Jakob Oren, Nesher (IL)

(73) Assignee: Bromine Compounds Ltd., Beer Sheva (IL)

( * ) Notice: Subject to any disclaimer, the term of this patent is extended or adjusted under 35 U.S.C. 154(b) by 0 days.

(21) Appl. No.: 14/429,817

(22) PCT Filed: Sep. 16, 2013

(86) PCT No.: PCT/IL2013/050784
§ 371 (c)(1),
(2) Date: Mar. 20, 2015

(87) PCT Pub. No.: WO2014/045278
PCT Pub. Date: Mar. 27, 2014

(65) Prior Publication Data
US 2015/0225318 A1    Aug. 13, 2015

Related U.S. Application Data

(60) Provisional application No. 61/704,586, filed on Sep. 24, 2012.

(51) Int. Cl.
*C07C 17/16* (2006.01)
*A01N 29/02* (2006.01)
*C07C 17/42* (2006.01)

(52) U.S. Cl.
CPC ............. *C07C 17/16* (2013.01); *A01N 29/02* (2013.01); *C07C 17/42* (2013.01)

(58) Field of Classification Search
CPC ......... C07C 17/16; C07C 17/42; A01N 29/02
See application file for complete search history.

(56) References Cited

U.S. PATENT DOCUMENTS

| 6,291,731 B1 * | 9/2001 | Stamm .................. C07C 17/16 570/217 |
| 6,777,375 B2 | 8/2004 | Magin et al. |
| 6,825,390 B1 | 11/2004 | Herndon |
| 2004/0044259 A1 * | 3/2004 | Mero ..................... C07C 17/16 570/261 |

FOREIGN PATENT DOCUMENTS

GB            942348       11/1963

OTHER PUBLICATIONS

International Search Report from PCT/IL2013/050784; 2 pages; mailed Sep. 1, 2014.

* cited by examiner

*Primary Examiner* — Shailendra Kumar
(74) *Attorney, Agent, or Firm* — Roach Brown McCarthy & Gruber, P.C.; Kevin D. McCarthy

(57) ABSTRACT

This invention provides a process for obtaining propargyl bromide in high yield from propargyl alcohol and phosphorus bromide, in the form of a stable composition with alkylbromide.

18 Claims, No Drawings

US 9,169,178 B2

MANUFACTURING OF STABILIZED PROPARGYL BROMIDE

This application is a 371 of PCT/IL13/50784, filed Sep. 16, 2013, which claims benefit of 61/704,586, filed Sep. 24, 2012.

FIELD OF THE INVENTION

The present invention relates to an industrial process for manufacturing propargyl bromide in a good yield and in a stable form.

BACKGROUND OF THE INVENTION

Methyl bromide is an effective fumigant used in controlling a large variety of soilborne pests. As methyl bromide is an ozone depleting agent, and further it is relatively toxic for humans, its use has been gradually reduced, and the demands for alternative pesticides have been increasing. A promising alternative for methyl bromide is 3-bromopropyne, usually called propargyl bromide (PB). PB may be prepared by the reaction of propargyl alcohol with $PBr_3$ in the presence of pyridine, but the selectivity and yield of the reaction are low. U.S. Pat. No. 6,794,551 improved the process by controlling temperature and effecting the reaction under an inert atmosphere without the presence of a base. Another problem about PB is its high flammability, and its vapors may form explosive mixtures with air. Precariously, propargyl bromide is a shock- and temperature-sensitive material that may detonate. Several techniques addressed the problem and stabilized PB by admixing a solvent forming an azeotropic mixture with the PB (see WO2004/071192; U.S. Pat. No. 6,777,375; U.S. Pat. No. 6,825,390; U.S. Pat. No. 7,015,367). It is an object of the present invention to provide an industrial process for manufacturing propargyl bromide in a stable form and in a good yield.

It is another object of the present invention to provide a composition comprising propargyl bromide in a sufficiently high concentration for intended applications but without being impact sensitive.

It is still another object of the present invention to provide a composition comprising propargyl bromide which is not explosive on heating.

Other objects and advantages of present invention will appear as description proceeds.

SUMMARY OF THE INVENTION

The invention provides a method for preparing a stable propargyl bromide (PB) composition, comprising i) combining propargyl alcohol (PA), an amine additive, and an alkylhalogenide (AH) source selected from halogenated paraffins and aliphatic alcohols; ii) adding phosphorus tribromide ($PBr_3$) to the mixture of step i) whereby obtaining a reaction mixture; iii) stirring said reaction mixture and allowing said $PBr_3$ to react at least with said PA, whereby obtaining a mixture containing raw PB and AH; and iv) washing the mixture of step iii) and distilling it at lowered pressure, wherein the steps of washing and distilling may be performed in any order, said washing comprising separating organic phase and discarding water phase; thereby obtaining a stable composition containing propargyl bromide and alkylhalogenide. Said AH source will usually include aliphatic materials having from 1 to 5 carbon atoms in the molecule. The term alkylhalogenide source aims at including both ready alkylhalogenide added to the mixture before the reaction starts, and a precursor of such alkylhalogenide which can be brominated by $PBr_3$ to provide the desired alkylhalogenide. The alkylhalogenide will usually include halogenated paraffins having from 1 to 5 carbon atoms in the molecule, the precursor will usually include aliphatic alcohols having from 3 to 5 carbon atoms in the molecule. The precursor will usually comprise a lower aliphatic alcohol like propanol or butanol, which will be brominated to the desired bromoalkane having the desired boiling point. In one aspect, the process according to the invention will comprise steps of i) mixing PA, an amine additive, and alkylhalogenide solvent having a boiling point between 55 and 110° C.; ii) adding $PBr_3$; iii) stirring the reaction mixture, and allowing said $PBr_3$ to react with said PA, whereby obtaining a mixture containing raw propargyl bromide and AH; and iv) washing and distilling said mixture in any order; thereby obtaining a stable composition containing propargyl bromide and alkylhalogenide. In other aspect of the invention, the process according to the invention will comprise i) mixing PA, an amine additive, and an aliphatic alcohol having between 3 and 5 carbon atoms; ii) adding $PBr_3$ whereby obtaining a reaction mixture; iii) stirring said reaction mixture and allowing said $PBr_3$ to react with said PA to provide PB, and with said alcohol to provide alkyl bromide (AB), wherein said AB has a boiling point between 55 and 110° C.; and iv) washing and distilling said mixture in any order; thereby obtaining a stable composition containing propargyl bromide and alkyl bromide. In a preferred embodiment, a method according to the invention comprises i) combining propargyl alcohol (PA), a tertiary amine, and an alkylhalogenide selected from chlorinated and/or brominated alkanes having a boiling point between 55 and 110° C., at a temperature between 0 and 40° C.; ii) adding $PBr_3$; iii) stirring the mixture obtained in step iii) at a temperature between 25 and 50° C. for between 1 and 5 hours, whereby obtaining a raw mixture containing PB and AH; iv) washing said raw mixture of step iii) with water; and v) distilling said raw mixture at lowered pressure at a temperature up to 60° C., wherein said step of washing and said step of distilling may be performed in any order; thereby obtaining a stable composition containing propargyl bromide and alkyl halogenide. In other preferred embodiment, a method according to the invention comprises i) combining PA, an amine additive, and an alkylbromide (AB) solvent having a boiling point between 55 and 110° C.; ii) adding $PBr_3$ whereby obtaining a reaction mixture; iii) stirring the reaction mixture of step ii), whereby obtaining a raw mixture containing PB and AB; iv) washing said raw mixture of step iii) with water; and v) distilling said raw mixture at lowered pressure at a temperature up to 60° C., wherein said step washing and said distilling may be performed in any order; thereby obtaining a stable composition containing propargyl bromide and alkyl bromide. Said amine additive is preferably a tertiary amine. Said stable composition, prepared by the method of the invention, usually comprises from 30 to 80 wt % propargylbromide, and it usually comprises from 17 to 67 wt % alkylhalogenide, for example from 19 to 69 wt % alkylhalogenide. In one embodiment of the invention, the stable composition prepared by the method of the invention comprises from 50 to 80 wt % propargylbromide, and it usually comprises from 17 to 47 wt % alkylhalogenide, for example from 19 to 49 wt % alkylhalogenide. The total amount of propargylbromide and alkylhalogenide in said stable composition is preferably at least 90 wt %, for example at least 94 wt %, such as 95 wt % or more.

In one embodiment of the method according to the invention, a process is provided comprising steps of i) mixing PA, an amine additive, and alkylbromide solvent having a boiling point between 55 and 110° C., and cooling the mixture to a temperature below 5° C. and adding dropwise PBr$_3$, under stirring, while keeping the temperature between 0 and 40° C.; ii) allowing said PBr$_3$ to react with said PA, whereby obtaining a mixture containing raw propargyl bromide and AH; and iii) washing and distilling said mixture in any order; thereby obtaining a stable composition containing propargyl bromide and alkylhalogenide. Said step ii) may comprise heating to a temperature of between 45 and 55° C., and stirring at this temperature for a time period of between 2 and 4 hours. Said step iii) may comprise adding water to the reaction mixture and cooling to ambient temperature. Said step iii) may comprise two washing steps, whereas the total water mass is usually less than the mass of the reaction mixture. Said step of distilling preferably comprises a vacuum of 100-250 mm Hg and a temperature of from 30 to 60° C.

In a method according to the invention, said alkylhalogenide may be, for example, propylbromide or butylbromide. Said amine additive may be, for example, triethylamine or pyridine. The yield of the process in the method of the invention is usually at least 70% based on PA. In some embodiments, said yield of reaction is at least 80%. The invention prepared by the above described method comprises, in one preferred embodiment, PB and AH, wherein said PB constitutes at least 55 wt %, and the total content of PB and AH is at least 92 wt % such as at least 98 wt %.

The invention provides a stable formulation for controlling soilborne pests, which contains propargyl bromide (PB) and alkyl bromide (AB), wherein the boiling points of said PB and AB differ by about 26° C. or less. In a preferred embodiment, the composition of the invention contains at least 55 wt % PB, and the total content of PB and AB at least 92 wt % such as 98 wt %.

DETAILED DESCRIPTION OF THE INVENTION

It has now been found that two problems associated with preparing propargyl bromide (PB), namely its explosiveness and the low yield obtained from propargyl alcohol (PA) and phosphorus tribromide (PBr$_3$), can be simultaneously solved by preparing the PB in a mixture comprising propargyl alcohol, an amine additive, and an alkylhalogenide solvent, such as alkylbromide (AB). Stable compositions comprising more than 50 wt % propargyl bromide were obtained by the reaction of PA and PBr$_3$ in bromopropane or bromobutane in the presence of triethylamine (TEA) as the amine additive. The reactions were carried out in a stirred reactor and the reaction progress was monitored by GC. The product formed a phase which was very easy to separate in the work-up stage. Moreover and very advantageously, no manipulations with PB are needed, as it is from the moment of its creation diluted with stabilizing solvent in the desired ratios. In one aspect of the invention, even the diluting solvent is created during the reaction, so that the desirable composition of PB and AB is created de novo from the basic reagents without need of manipulations with these components and their mixing.

After full conversion of PA (>99%) the reaction mixture was usually cooled, water was added and the phases were separated. The organic phase was washed with water, and the mixture of PB and AB was separated by fractional distillation at lowered pressure, such that the temperature during the distillation did not rise above 60° C. The yield of the process of obtaining PB in this stage was usually ~70% based on PA.

In a first aspect of the invention, said alkylhalogenide solvent is a halogenated paraffin, incorporated to the reaction mixture with other reagents, having boiling point not too different from the boiling point of PB. In a second aspect of the invention, said alkylhalogenide is a brominated paraffin, having boiling point not too different from the boiling point of PB, formed in the reaction mixture during the reaction together with the PB. When relating to the boiling point of a suitable alkylhalogenide, the boiling points of PB and said solvent are considered as too different when they differ by more than about 26° C.; a suitable solvent for the present invention will have a boiling point between 55 and 110° C., taking into consideration that boiling points are usually provided with a precision ±2° C. In said first aspect of the invention, said alkylhalogenide solvent may comprise C$_1$-C$_5$ alkane having one or more atoms substituted with one or two halogen elements. Said halogen in said solvent may comprise fluorine, an example being tetrachlorodifluoroethane. Said halogen may comprise iodine, an example being 2-iodopropane. However, because of practical reasons, said solvent preferably comprises chlorine or bromine, since other halogens may be excluded from some applications: fluorine mostly due to environmental considerations, and iodine due to lower stability and possibly higher toxicity. The solvent suitable for the invention preferably comprises aliphatic hydrocarbon substituted with one or more chlorine and/or bromine atoms.

In one embodiment of the invention, the solvent diluting propargyl bromide comprises a chlorinated paraffin such as, for example, dichloroethane, trichloroethane, dichloropropane, chlorobutane, chloromethylpropane, chloropentane.

In a preferred embodiment of the invention, the solvent diluting propargyl bromide comprises a brominated paraffin (or alkyl bromide, AB) such as, for example, dibromomethane, bromopropane, bromobutane, bromomethylpropane, or bromomethylbutane.

In another embodiment of the invention, the solvent diluting propargyl bromide comprises a brominated and chlorinated paraffin such as, for example, bromochloroethane or bromochloromethane.

In one embodiment of the invention, the solvent is a mixture of more isomers or more different compounds, possibly selected from the above recited brominated and/or chlorinated solvents. The solvent has a diluting and stabilizing role, but it will often further improve the action of PB in certain application and may even contribute to synergistic effects.

The chemical reaction for the preparation of PB is presented in the following scheme, in which TEA may be replaced by other amine additive like pyridine, and RBr stands for a source of brominated alkane:

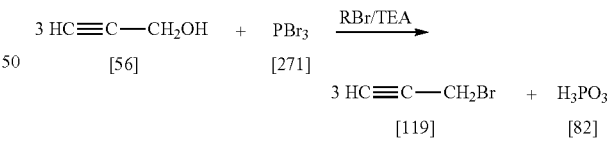

The competing reaction in the preparation of PB is the addition of HBr to the PB to form 2,3-dibromopropene (major) and 1,3-dibromopropene (minor). These side products are formed in an amount of less than 10%, such as less than 6%. These side product are formed in lower amounts in the method according to the invention, when compared with the published methods in which the formation of side products in amounts 13 wt % and more is usual (compare, for example, U.S. Pat. No. 6,794,551). The term "source of brominated alkane" stands for the brominated alkane itself or for a compound which reacts with PBr$_3$ to provide a brominated alkane; such compound may comprise an aliphatic alcohol, such as propanol or butanol. In some embodiments, a mixture of solvents may be involved. Said solvent may be advantageously 2-bromobutane and said amine triethyl amine.

When processing the reaction products, it is possible to wash the reaction mixture and then distill the organic phase, or firstly distill the mixture and then wash with water; each way has its advantages and disadvantages, as a skilled person will acknowledge. The reactants may be combined in a batch reactor under stirring and under controlled temperature, while one or more reactant may be present from the beginning in the reactor and one or more other reactants may be gradually dosed to the reactor. In one embodiment, the reactants are combined as two or more liquid streams. In one aspect of the invention, the process of the invention works in a batch mode. In other aspect, the process of the invention works in a continuous mode. The process of the invention comprises bromination of at least propargyl alcohol, and possibly simultaneously also an additional component selected from alcohols, such as $C_3$-$C_5$ alcohols: propargyl alcohol provides propargyl bromide and said other component provides the stabilizing brominated solvent.

In a preferred embodiment, the brominating agent is phosphorus tribromide in a molar excess usually of 2-10% over the reactant(s), such as 5%. Said amine is usually present in an amount of between 5 and 25 molar % of the used PA, preferably about 15-20 molar %. PA in a brominated solvent will react with phosphorus tribromide at the presence of said amine, the PB usually constituting between 50 wt % and 80 wt % of the final mixture of PB and halogenated solvent. The reaction usually takes from 1 to 5 hours to full conversion of PA (>99%), for example 3 hours. For example, when performing the process in a batch mode, and when employing 2-Br-butane as the solvent, the solvent and the PA are placed in the reactor in a mass ratio of between 1/3 and 2/1 and the brominated agent is added during about 1.5-3 hours at a temperature between 0 and 40° C., after which the reaction mixture is stirred and left to finish the reaction for 1-3 more hours at a temperature between 25 and 50° C. The reactor should preferably be provided with temperature control, the reaction being preferably cooled at the stage of reagent addition, and kept at higher temperature for completing the reaction. The reaction mixture may be distilled, before or after washing with water, to obtain product of PB and halogenated solvent, preferably alkyl bromide (AB). The distillation comprises lowered pressure, such as for example between 100 and 250 mm Hg, and a temperature between, for example, 30 and 60° C. Washing may comprise, for example, one or more steps of mixing with water in a total amount of, for example, 10-30 wt % of the reaction mixture. The halogenated solvent may comprise a chloro or bromo alkane having a boiling point within about ±26° C. of the propargyl bromide (PB) boiling point, examples comprising bromochloromethane, dibromomethane, 1,2-dichloroethane, bromochloroethane, 1-bromopropane, 1-chloro-2-methylpropane, 1-chlorobutane, bromobutane, 1-bromo-2-methylpropane, or chloropentane. In a preferred embodiment, the solvent comprises alkylhalogenide having a boiling point within about +20° C. of the boiling point of propargyl bromide, namely between about 60 and about 104° C., the examples comprising methylene bromide, ethylene dichloride, 1-bromo-1-chloroethane, isobutyl bromide, 1-bromopropane, 2-bromobutane, 1-bromobutane, 2-bromo-2-methylbutane, or 2-chloropentane. The solvent may comprise a mixture of more halogenated alkanes.

The process of the invention provides a good yield of concentrated product of propargyl bromide with a stabilizing amount of alkyl bromide. In typical products, PB is at least 55 wt %, for example about 80 wt %. In one embodiment of the invention, the method of the invention provides a concentrated product comprising PB and stabilizing alkylbromide, wherein said PB comprises at least 55 wt %, and the sum of said PB and said alkyl bromide comprises at least 95 wt %, and wherein the yield of the reaction is at least 80%.

The invention thus provides a process for manufacturing a composition comprising stabilized propargyl bromide (PB), which composition comprises beside PB one or more solvents of similar physical properties as PB, and in special cases the solvent has also suitable biological properties, which is advantageously utilized in various applications, the example being fumigation.

EXAMPLES

Reagents and Methods

Propargyl alcohol, 1-Bromobutane, 2-Bromopropane, 1-Bromopropane, 2-Bromobutane, 1-Bromo-2-Methylpropane, 2-Butanol, Pyridine, Phosphorus tribromide were obtained from Aldrich, Triethylamine from Merck.
GC: Gas-chromatograph HP 7890A
Program (PROPBR method):
Initial temp. 50° C., held 7 min, then raised to 300° C. at 15° C./min and held 3 mins.
Injector: 250° C.
Detector: 300° C.
Split ratio: 1:100
Injection amounts: 0.3 µl
Column: Quadrex, capillary, 30 m×0.25 mm×0.25µ, 007 Series Methyl Silicone
The retention times of the components are as follows:

| | |
|---|---|
| 2-Bromopropane | 2.9-3.0 min |
| 1-Bromopropane | 3.2-3.3 min |
| Propargyl bromide | 3.4-3.6 min |
| 2-Bromobutane | 4.0-4.2 min |
| 1-Bromobutane | 4.8-4.9 min |
| 2,3-Dibromopropene | 8.6-9.1 min |
| 1,3-Dibromopropene | 9.9-10.0 min |

1H-NMR spectra were taken on an AVANCE III, 500 MHz Bruker instrument.

Example 1

Preparation of Propargyl Bromide in 1-Bromobutane
(Run 8 and 12)

Into a 0.5 L reactor equipped with a mechanical stirrer, a thermocouple, a dropping funnel and a condenser connected to a scrubber system, reagents were placed: 1-bromobutane (30 g), propargyl alcohol (33.6 g) and triethylamine (9.1 g), at room temperature, with stirring. The contents of the reactor were cooled to 0° C. and $PBr_3$ (57 g) was added dropwise, with mechanical stirring, over 1 h, such that the temperature in the reactor did not rise above 5° C. After completion of the addition, the reactor contents were heated to 50° C. over 1 h then held at this temperature for 3 h with stirring. Water (35 g) was added to the reaction mixture with cooling to room temperature. The phases were separated, the organic phase was washed with water (35 g) and the phases were separated. A mixture containing propargyl bromide and 1-bromobutane (79 g) was obtained by fractional distillation of the organic phase in a vacuum of 160→150 mmHg and a temperature in the reactor of 44→45° C.

The composition of the product was determined by GC and GC/MS analysis and NMR: Propargyl bromide: 63.5% by GC area %, about 65% by 1H-NMR; 1-Bromobutane: 35.9% by GC area %, about 34% by 1H-NMR.

Example 2

Preparation of Propargyl Bromide in 2-Bromopropane (9 and 13)

Into a 0.5 L reactor equipped with a mechanical stirrer, a thermocouple, a dropping funnel and a condenser connected to a scrubber system, reagents were placed: 2-bromopropane (30 g), propargyl alcohol (56 g) and triethylamine (15 g), at room temperature, with stirring. The contents of the reactor were cooled to 0° C. and PBr$_3$ (95 g) was added dropwise, with mechanical stirring, over 1.5 h, such that the temperature in the reactor did not rise above 5° C. After completion of the addition, the reactor contents were heated to 50° C. over 1.5 h then held at this temperature for 3 h with stirring. Water (35 g) was added to the reaction mixture with cooling to room temperature. The phases were separated, the organic phase was washed with water (35 g) and the phases were separated. A mixture containing propargyl bromide and 2-bromopropane (108 g) was obtained by fractional distillation of the organic phase in a vacuum of 175→145 mmHg and a temperature in the reactor of 36→55° C.

The composition of the product was determined by GC and GC/MS analysis and NMR: Propargyl bromide: 78.9% by GC area %, about 81% by 1H-NMR; 2-Bromopropane: 20.6% by GC area %, about 18% by 1H-NMR.

Example 3

Preparation of Propargyl Bromide in 1-Bromopropane (Run 10 and 14)

Into a 0.5 L reactor equipped with a mechanical stirrer, a thermocouple, a dropping funnel and a condenser connected to a scrubber system, reagents were placed: 1-bromopropane (30 g), propargyl alcohol (56 g) and triethylamine (15 g), at room temperature, with stirring. The contents of the reactor were cooled to 0° C. and PBr$_3$ (95 g) was added dropwise, with mechanical stirring, over 1.5 h, such that the temperature in the reactor did not rise above 5° C.

After completion of the addition, the reactor contents were heated to 50° C. over 1.5 h then held at this temperature for 3 h with stirring. Water (35 g) was added to the reaction mixture with cooling to room temperature. The phases were separated, the organic phase was washed with water (35 g) and the phases were separated. A mixture containing propargyl bromide and 1-bromopropane (111 g) was obtained by fractional distillation of the organic phase in a vacuum of 170→120 mmHg and a temperature in the reactor of 37→57° C.

The composition of the product was determined by GC and GC/MS analysis and NMR: Propargyl bromide: 82.3% by GC area %, about 83% by 1H-NMR; 1-Bromopropane: 17.0% by GC area %, about 16% by 1H-NMR.

Example 4

Preparation of Propargyl Bromide in 2-Bromobutane (Run 11 and 15)

Into a 0.5 L reactor equipped with a mechanical stirrer, a thermocouple, a dropping funnel and a condenser connected to a scrubber system, reagents were placed: 2-bromobutane (30 g), propargyl alcohol (56 g) and triethylamine (15 g), at room temperature, with stirring. The contents of the reactor were cooled to 0° C. and PBr$_3$ (95 g) was added dropwise, with mechanical stirring, over 1.5 h, such that the temperature in the reactor did not rise above 5° C. After completion of the addition, the reactor contents were heated to 50° C. over 1.5 h then held at this temperature for 3 h with stirring. Water (35 g) was added to the reaction mixture with cooling to room temperature. The phases were separated, the organic phase was washed with water (35 g) and the phases were separated. A mixture containing propargyl bromide and 2-bromobutane (110 g) was obtained by fractional distillation of the organic phase in a vacuum of 130→120 mmHg and a temperature in the reactor of 37→57° C.

The composition of the product was determined by GC and GC/MS analysis and NMR: Propargyl bromide: 72.8% by GC area %, about 75% by 1H-NMR; 2-Bromobutane: 26.7% by GC area %, about 24% by 1H-NMR.

Example 5

Preparation of Propargyl Bromide in 2-Bromobutane (Run 18)

Into a 0.5 L reactor equipped with a mechanical stirrer, a thermocouple, a dropping funnel and a condenser connected to a scrubber system, reagents were placed: 2-bromobutane (50 g), propargyl alcohol (112 g) and triethylamine (30 g), at room temperature, with stirring. The contents of the reactor were cooled to 10° C. and PBr3 (190 g) was added dropwise, with mechanical stirring, over 2 h, such that the temperature in the reactor did not rise above 20° C. After completion of the addition, the reactor contents were heated to 50° C. over 1 h, then held at this temperature for 3 h with stirring. Water (70 g) was added to the reaction mixture with cooling to room temperature. The phases were separated, the organic phase was washed with water (35 g) and the phases were separated. A mixture containing propargyl bromide and 2-bromobutane (216 g) was obtained by fractional distillation of the organic phase in a vacuum of 150→120 mmHg and a temperature in the reactor of 35→56° C.

The composition of the product was determined by GC analysis and NMR: Propargyl bromide 76.5% by GC area %, ~78% by 1H-NMR; 2-Bromobutane 22.6% by GC area %, ~21% by 1H-NMR.

Example 6

Preparation of Propargyl Bromide in 2-Bromobutane (Run 19)

Into a 0.5 L reactor equipped with a mechanical stirrer, a thermocouple, a dropping funnel and a condenser connected to a scrubber system, reagents were placed: 2-bromobutane (50 g), propargyl alcohol (112 g), and pyridine (30 g), at room temperature, with stirring. The contents of the reactor were cooled to 10° C. and PBr3 (190 g) was added dropwise, with mechanical stirring, over 1.5 h, such that the temperature in the reactor did not rise above 20° C. After completion of the addition, the reactor contents were heated to 50° C. over 1.5 h then held at this temperature for 3 h with stirring. Water (70 g) was added to the reaction mixture with cooling to room temperature. The phases were separated, the organic phase was washed with water (35 g) and the phases were separated. A mixture containing propargyl bromide and 2-bromobutane (215 g) was obtained by fractional distillation of the organic phase in a vacuum of 150→120 mmHg and a temperature in the reactor of 35→56° C.

The composition of the product was determined by GC analysis and NMR: Propargyl bromide 76.6% by GC area %, 78% by 1H-NMR; 2-Bromobutane 22.7% by GC area %; ~21% by 1H-NMR.

Example 7

Preparation of Propargyl Bromide in 1-Bromopropane (Run 20)

Into a 0.5 L reactor equipped with a mechanical stirrer, a thermocouple, a dropping funnel and a condenser connected to a scrubber system, reagents were placed: 1-bromopropane (50 g), propargyl alcohol (112 g), and pyridine (30 g), at room temperature, with stirring. The contents of the reactor were cooled to 11° C. and PBr3 (190 g) was added dropwise, with mechanical stirring, over 1.5 h, such that the temperature in the reactor did not rise above 20° C. After completion of the addition, the reactor contents were heated to 50° C. over 1 h then held at this temperature for 3 h with stirring. Water (70 g) was added to the reaction mixture with cooling to room temperature. The phases were separated, the organic phase was washed with water (35 g) and the phases were separated. A mixture containing propargyl bromide and 1-bromopropane (212 g) was obtained by fractional distillation of the organic phase in a vacuum of 140→110 mmHg and a temperature in the reactor of 30→60° C.

The composition of the product was determined by GC analysis and NMR: Propargyl bromide 76.6% by GC area %, ~77% by 1H-NMR; 1-Bromopropane 22.5% by GC area %, ~22% by 1H-NMR.

Example 8

Preparation of Propargyl Bromide in 1-Bromopropane (Run 21)

Into a 0.5 L reactor equipped with a mechanical stirrer, a thermocouple, a dropping funnel and a condenser connected to a scrubber system, reagents were placed: 1-bromopropane (50 g), propargyl alcohol (112 g) and triethylamine (30 g), at room temperature, with stirring. The contents of the reactor were cooled to 14° C. and PBr3 (190 g) was added dropwise, with mechanical stirring, over 1.5 h, such that the temperature in the reactor did not rise above 20° C. After completion of the addition, the reactor contents were heated to 50° C. over 1 h then held at this temperature for 3 h with stirring. Water (70 g) was added to the reaction mixture with cooling to room temperature. The phases were separated, the organic phase was washed with water (35 g) and the phases were separated. A mixture containing propargyl bromide and 1-bromopropane (213 g) was obtained by fractional distillation of the organic phase in a vacuum of 140→110 mmHg and a temperature in the reactor of 30→60° C.

The composition of the product was determined by GC analysis and NMR: Propargyl bromide 76.5% by GC area %, ~77% by 1H-NMR; 1-Bromopropane 22.6% by GC area %, ~22% by 1H-NMR.

Example 9

Preparation of Propargyl Bromide in 1-Bromopropane (Run 26)

Into a 0.5 L reactor equipped with a mechanical stirrer, a thermocouple, a dropping funnel and a condenser connected to a scrubber system, reagents were placed: 1-bromopropane (50 g), propargyl alcohol (112 g), and triethylamine (30 g) at room temperature, with stirring. The contents of the reactor were cooled to 10° C., and PBr3 (190 g) was added dropwise, with mechanical stirring, over 1.5 h, such that the temperature in the reactor did not rise above 20° C. After completion of the addition, the reactor contents were heated to 50° C. over 1 h then held at this temperature for 3 h with stirring. A mixture containing propargyl bromide and 1-bromopropane (207 g) was obtained by fractional distillation of the reaction mixture in a vacuum of 145→120 mmHg and a temperature in the reactor of 36→58° C., followed by washing with water (50 g) and the phases separation.

The composition of the product was determined by GC analysis and NMR: Propargyl bromide 79.6% by GC area %, ~76% by 1H-NMR; 1-Bromopropane 19.7% by GC area %, ~23% by 1H-NMR.

Example 10

Preparation of Propargyl Bromide in 2-Butanol (Run 28)

Into a 0.5 L reactor equipped with a mechanical stirrer, a thermocouple, a dropping funnel and a condenser connected to a scrubber system, reagents were placed: 2-butanol (27 g), propargyl alcohol (112 g) and triethylamine (35 g), at room temperature, with stirring. The contents of the reactor were cooled to 10° C., and PBr3 (225 g) was added dropwise, with mechanical stirring, over 2 h, such that the temperature in the reactor did not rise above 20° C. After completion of the addition, the reactor contents were heated to 50° C. over 1 h then held at this temperature for 2.5 h with stirring. Water (70 g) was added to the reaction mixture with cooling to room temperature. The phases were separated, the organic phase was washed with water (35 g) and the phases were separated. A mixture containing propargyl bromide and 2-bromobutane (210 g) was obtained by fractional distillation of the organic phase in a vacuum of 150→120 mmHg and a temperature in the reactor of 35→60° C.

The composition of the product was determined by GC analysis and NMR: Propargyl bromide—77.6% by GC area %, ~80% by 1H-NMR; 2-Bromobutane 21.5% by GC area %, ~18% by 1H-NMR.

Example 11

Preparation of Propargyl Bromide in 2-Bromobutane (Run 32)

Into a 0.5 L reactor equipped with a mechanical stirrer, a thermocouple, a dropping funnel and a condenser connected to a scrubber system, reagents were placed: 2-bromobutane (50 g), propargyl alcohol (112 g), and TEA (30 g), at room temperature, with stirring. PBr3 (190 g) was added dropwise, with mechanical stirring, over 1.5 h, such that the temperature in the reactor did not rise above 40° C. After completion of the addition, the reactor contents were heated to 50° C. over 1.5 h then held at this temperature for 3 h with stirring. Water (70 g) was added to the reaction mixture with cooling to room temperature. The phases were separated, the organic phase was washed with water (35 g) and the phases were separated. A mixture containing propargyl bromide and 2-bromobutane (212 g) was obtained by fractional distillation of the organic phase in a vacuum of 160→120 mmHg and a temperature in the reactor of 35→60° C.

The composition of the product was determined by GC analysis and NMR: Propargyl bromide 77.4% by GC area %, 79% by 1H-NMR; 2-Bromobutane 21.6% by GC area %; ~20% by 1H-NMR.

Example 12

Preparation of Crude Propargyl Bromide in 2-Bromobutane (Run 39)

Into a 0.5 L reactor equipped with a mechanical stirrer, a thermocouple, a dropping funnel and a condenser connected to a scrubber system were placed 2-bromobutane (168 g), propargyl alcohol (168 g) and triethylamine (45 g) at room temperature, with stirring. The contents of the reactor were cooled to 10° C. and $PBr_3$ (285 g) was added dropwise, with mechanical stirring, over 2 h, such that the temperature in the reactor did not rise above 20° C. After completion of the addition, the reactor contents were heated to 50° C. over 1 h then held at this temperature for 3 h. Water (90 g) was added to the reaction mixture with cooling to room temperature. The phases were separated, the organic phase was washed with water (60 g) and the phases were separated.

The composition of the crude product (473 g) was determined by GC analysis:

| | |
|---|---|
| Propargyl bromide | 55.0% by GC area % |
| 2-Bromobutane | 39.0% by GC area % |
| 2,3-Dibromopropene | 4.4% by GC area % |
| 1,3-Dibromopropene | 0.8% by GC area % |

Example 13

Preparation of Crude Propargyl Bromide in 2-Bromobutane (Run 40)

Into a 0.5 L reactor equipped with a mechanical stirrer, a thermocouple, a dropping funnel and a condenser connected to a scrubber system were placed 2-bromobutane (168 g), propargyl alcohol (168 g) and triethylamine (45 g) at room temperature, with stirring. The contents of the reactor were cooled to 10° C. and $PBr_3$ (190 g) was added dropwise, with mechanical stirring, over 2 h, such that the temperature in the reactor did not rise above 20° C. After completion of the addition, the reactor contents were heated to 50° C. over 1 h then held at this temperature for 3.5 h. Water (90 g) was added to the reaction mixture with cooling to room temperature. The phases were separated, the organic phase was washed with water (60 g) and the phases were separated.

The composition of the crude product (474 g) was determined by GC analysis:

| | |
|---|---|
| Propargyl bromide | 54.3% by GC area % |
| 1-Bromopropane | 39.1% by GC area % |
| 2,3-Dibromopropene | 4.9% by GC area % |
| 1,3-Dibromopropene | 0.8% by GC area % |

Example 14

Preparation of Pure Propargyl Bromide Solution in 2-Bromobutane (Runs 43 and 46)

A part of the organic phases of two experiments (39697-39 and 40) were combined (total 932 g) and their acidity was neutralized with aq. 1% $NaHCO_3$ (114 g). The phases were separated and the organic phase (925 g) underwent fractional distillation with the aid of a 15 cm high column filled with Raschig rings. The solution of pure Prop-Br in 2-BB was obtained in the fraction obtained under the conditions of 150→135 mmHg vacuum and distillation head temperature of 37.4-39.6° C. During the distillation, the wall temperature was 80° C. and the temperature of the solution rose from 40° C. to 50° C.

The composition of the pure Prop-Br in 2-BB (787 g) was determined by GC and $^1$H-NMR analysis:

| | |
|---|---|
| Propargyl bromide | 58.9% by GC, area %; ~59% by $^1$H-NMR |
| 2-Bromobutane | 40.5% by GC, area %; ~41% by $^1$H-NMR |

Example 15

Preparation of Crude Propargyl Bromide in 1-Bromo-2-Methylpropane (Run 41)

Into a 0.5 L reactor equipped with a mechanical stirrer, a thermocouple, a dropping funnel and a condenser connected to a scrubber system were placed 1-bromo-2-methylpropane (112 g), propargyl alcohol (112 g) and triethylamine (30 g) at room temperature, with stirring. The contents of the reactor were cooled to 15° C. and $PBr_3$ (190 g) was added dropwise, with mechanical stirring, over 2 h, such that the temperature in the reactor did not rise above 20° C. After completion of the addition, the reactor contents were heated to 50° C. over 1 h then held at this temperature for 3 h. Water (60 g) was added to the reaction mixture with cooling to room temperature. The phases were separated, the organic phase was washed with water (40 g) and the phases were separated.

The composition of the crude product (312 g) was determined by GC analysis:

| | |
|---|---|
| Propargyl bromide | 54.8% by GC area % |
| 1-Bromo-2-methylpropane | 39.7% by GC area % |
| 2,3-Dibromopropene | 4.1% by GC area % |
| 1,3-Dibromopropene | 0.7% by GC area % |

Example 16

Preparation of Crude Propargyl Bromide in 1-Bromo-2-Methylpropane (Run 44)

Into a 0.5 L reactor equipped with a mechanical stirrer, a thermocouple, a dropping funnel and a condenser connected to a scrubber system were placed 1-bromo-2-methylpropane (168 g), propargyl alcohol (168 g) and triethylamine (45 g) at room temperature, with stirring. The contents of the reactor were cooled to 11° C. and $PBr_3$ (285 g) was added dropwise, with mechanical stirring, over 2 h, such that the temperature in the reactor did not rise above 20° C.

After completion of the addition, the reactor contents were heated to 50° C. over 1 h then held at this temperature for 3 h. Water (90 g) was added to the reaction mixture with cooling to room temperature. The phases were separated, the organic phase was washed with water (60 g) and the phases were separated.

The composition of the crude product (473 g) was determined by GC analysis:

| | |
|---|---|
| Propargyl bromide | 55.9% by GC area % |
| 1-Bromo-2-methylpropane | 38.6% by GC area % |
| 2,3-Dibromopropene | 4.0% by GC area % |
| 1,3-Dibromopropene | 0.7% by GC area % |

Example 17

Preparation of Pure Propargyl Bromide Solution in 1-Bromo-2-Methylpropane (Run 47)

A part of the organic phases of two experiments (41 and 44) were combined (total 771 g) and their acidity was neutralized with aq. 1% NaHCO$_3$ (118 g). The phases were separated and the organic phase (766 g) underwent fractional distillation with the aid of a 15 cm high column filled with Raschig rings. The solution of pure Prop-Br in 1-Br-2-MP was obtained in the fraction obtained under the conditions of 180→160 mmHg vacuum and distillation head temperature of 43.3-47.2° C. During the distillation, the wall temperature was 80° C. and the temperature of the solution rose from 47° C. to 55° C.

The composition of the pure Prop-Br in 2-BB (652 g) was determined by GC and $^1$H-NMR analysis:

| | |
|---|---|
| Propargyl bromide | 59.2% by GC, area %; ~60% by $^1$H-NMR |
| 1-Bromo-2-methylpropane | 40.3% by GC, area %; ~40% by $^1$H-NMR |

While the invention has been described using some specific examples, many modifications and variations are possible. It is therefore understood that the invention is not intended to be limited in any way, other than by the scope of the appended claims.

The invention claimed is:

1. A method for preparing a stable propargyl bromide (PB) composition, comprising
   i) combining propargyl alcohol (PA), an amine additive, and an alkylhalogenide (AH) source selected from halogenated paraffins and aliphatic alcohols, whereby obtaining a liquid mixture;
   ii) adding phosphorus tribromide (PBr3) to the mixture of step i) whereby obtaining a reaction mixture;
   iii) stirring said reaction mixture of step ii) and allowing said PBr3 to react at least with said PA, whereby obtaining a mixture containing raw PB and AH; and
   iv) washing the mixture of step iii) and distilling it at lowered pressure, wherein the steps of washing and distilling may be performed in any order, wherein said washing comprises separating organic phase and discarding water phase;
   thereby obtaining a stable composition containing propargyl bromide and alkylhalogenide.

2. A method according to claim 1, comprising
   i) combining PA, an amine additive, and alkylhalogenide solvent having a boiling point between 55 and 110° C., whereby obtaining a liquid mixture;
   ii) adding PBr3 to the mixture of step i) whereby obtaining a reaction mixture;
   iii) stirring said reaction mixture of step ii) and allowing said PBr3 to react with said PA, whereby obtaining a mixture containing raw propargyl bromide and AH; and
   iv) washing and distilling said mixture in any order;
   thereby obtaining a stable composition containing propargyl bromide and alkylhalogenide.

3. A method according to claim 1, comprising
   i) combining PA, an amine additive, and an aliphatic alcohol having between 3 and 5 carbon atoms, whereby obtaining a liquid mixture;
   ii) adding PBr3 to said mixture of step i) whereby obtaining a reaction mixture;
   iii) stirring said reaction mixture and allowing said PBr3 to react with said PA to provide PB, and with said aliphatic alcohol to provide alkyl bromide (AB), wherein said AB has a boiling point between 55 and 110° C.; and
   iv) washing and distilling said mixture in any order;
   thereby obtaining a stable composition containing propargyl bromide and alkyl bromide.

4. A method according to claim 1, comprising
   i) combining propargyl alcohol (PA), an amine additive, and an alkylhalogenide selected from chlorinated and/or brominated alkanes having a boiling point between 55 and 110° C., whereby obtaining a liquid mixture;
   ii) adding PBr3 to the mixture of step i) whereby obtaining a reaction mixture;
   iii) stirring said reaction mixture of step ii) for between 1 and 5 hours and allowing said PBr3 to react with said PA to provide PB, whereby obtaining a raw mixture containing PB and AH;
   iv) washing said raw mixture of step iii) with water; and
   v) distilling said raw mixture at lowered pressure at a temperature of between 30 and 60° C., wherein said step of washing and said step of distilling may be performed in any order;
   thereby obtaining a stable composition containing propargyl bromide and alkyl halogenide.

5. A method according to claim 1, comprising
   i) combining PA, an amine additive, and an alkylbromide (AB) solvent having a boiling point between 55 and 110° C., at a temperature between 0 and 40° C., whereby obtaining a liquid mixture;
   ii) adding PBr3 to the mixture of step i) whereby obtaining a reaction mixture;
   iii) stirring said reaction mixture of step ii) at a temperature between 25 and 50° C. and allowing said PBr3 to react with said PA whereby obtaining a raw mixture containing PB and AB;
   iv) washing said raw mixture of step iii) with water; and
   v) distilling said raw mixture at lowered pressure at a temperature of 30-60° C., wherein said step washing and said distilling may be performed in any order;
   thereby obtaining a stable composition containing propargyl bromide and alkyl bromide.

6. A method according to claim 1, wherein said AH source is selected from halogenated paraffins having from 1 to 5 carbon atoms in the molecule and aliphatic alcohols having from 3 to 5 carbon atoms in the molecule.

7. A method according to claim 1, wherein said amine additive is a tertiary amine.

8. A method according to claim 1, wherein said stable composition comprises from 30 to 80 wt % propargylbromide, and from 17 to 67 wt % alkylhalogenide.

9. A method according to claim 1, wherein said stable composition comprises from 30 to 80 wt % propargylbromide, and from 19 to 69 wt % alkylhalogenide.

10. A method according to claim 1, wherein said stable composition comprises propargylbromide and alkylhalogenide in a total amount of at least 90 wt %.

11. A method according to claim 1, wherein said stable composition comprises propargylbromide and alkylbromide in a total amount of at least 99 wt %.

12. A method according to claim 2, wherein said step i) comprises cooling the mixture to a temperature below 5° C., wherein said step ii) comprises adding dropwise PBr3 under stirring while keeping the temperature between 5 and 40° C., and wherein said step iii) comprises heating to a temperature of between 45 and 55° C., and stirring at this temperature for a time period of between 2 and 4 hours.

13. A method according to claim 2, wherein said step iv) comprises adding water to the reaction mixture and cooling to ambient temperature.

14. A method according to claim 2, wherein said step iv) comprises two washing steps.

15. A method according to claim 2, wherein said step of distilling comprises a vacuum of between 100 and 250 mm Hg and a temperature of between 30 and 60° C.

16. A method according to claim 1, wherein alkylhalogenide is selected from propylbromides, butylbromides, and pentylbromides.

17. A method according to claim 1, wherein said amine additive is triethylamine or pyridine.

18. A method according to claim 1, wherein the yield of the reaction based on PA is at least 80%.

* * * * *